US012221601B2

(12) United States Patent
Papas (10) Patent No.: US 12,221,601 B2
(45) Date of Patent: *Feb. 11, 2025

(54) METHODS AND SYSTEMS FOR REAL-TIME ASSESSMENT OF CELLS IN ENCAPSULATION DEVICES PRE-AND POST-TRANSPLANTATION

(71) Applicant: Arizona Board of Regents on Behalf of the University of Arizona, Tucson, AZ (US)

(72) Inventor: Klearchos K. Papas, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/230,996

(22) Filed: Aug. 7, 2023

(65) Prior Publication Data

US 2023/0383231 A1 Nov. 30, 2023

Related U.S. Application Data

(63) Continuation of application No. 16/347,147, filed as application No. PCT/US2017/060041 on Nov. 3, 2017, now Pat. No. 11,746,318.

(Continued)

(51) Int. Cl.
*C12M 1/34* (2006.01)
*C12M 1/00* (2006.01)
(Continued)

(52) U.S. Cl.
CPC ........... *C12M 41/34* (2013.01); *C12M 25/02* (2013.01); *C12M 29/00* (2013.01); *C12M 41/18* (2013.01);
(Continued)

(58) Field of Classification Search
None
See application file for complete search history.

(56) References Cited

U.S. PATENT DOCUMENTS

| | | |
|---|---|---|
| 4,902,476 A | 2/1990 | Gordon et al. |
| 5,169,390 A | 12/1992 | Athayde et al. |

(Continued)

FOREIGN PATENT DOCUMENTS

| | | | |
|---|---|---|---|
| CA | 2985753 A1 * | 9/2014 | ............ A61K 35/39 |
| CA | 3042709 | 8/2018 | |
| CN | 101123984 | 2/2008 | |
| CN | 201337642 | 11/2009 | |
| CN | 102012390 | 4/2011 | |
| CN | 203915611 | 11/2014 | |
| CN | 105163688 | 12/2015 | |
| CN | 105792775 | 7/2016 | |

(Continued)

OTHER PUBLICATIONS

U.S. Appl. No. 18/142,368, filed May 2, 2023, Papas et al.
(Continued)

*Primary Examiner* — Holly Kipouros
(74) *Attorney, Agent, or Firm* — Sheridan Ross P.C.

(57) ABSTRACT

Methods and systems for measuring viability and function of islet cells or stem cell-derived beta cells in an implantable device featuring setting the temperature of the cells in the implantable device to a low temperature to reduce metabolic levels of the cells and reduce oxygen requirements of the cells, and measuring oxygen consumption rates. An oxygen sensor at the inlet of the implantable device and an oxygen sensor at the outlet of the implantable device are used to calculate oxygen consumption rates of the cells, which in turn are indicative of viability. The reduction in temperature can also be used for loading cells into the implantable devices to help reduce ischemic and/or physical injury. The present invention may be used with other cell types, e.g. hepatocytes, heart cells, muscle cells, etc.

9 Claims, 4 Drawing Sheets

Related U.S. Application Data (60) Provisional application No. 62/417,039, filed on Nov. 3, 2016.

(51) Int. Cl.
  *C12M 1/02* (2006.01)
  *C12M 1/12* (2006.01)
  *C12N 5/071* (2010.01)

(52) U.S. Cl.
  CPC ............ *C12M 41/26* (2013.01); *C12M 41/32* (2013.01); *C12N 5/0676* (2013.01); *C12N 2500/02* (2013.01)

(56) References Cited

U.S. PATENT DOCUMENTS

| | | | |
|---|---|---|---|
| 5,324,518 A | 6/1994 | Orth et al. | |
| 5,368,028 A | 11/1994 | Palti | |
| 5,595,621 A | 1/1997 | Light et al. | |
| 5,626,561 A | 5/1997 | Butler et al. | |
| 5,713,888 A | 2/1998 | Brauker et al. | |
| 5,741,330 A | 4/1998 | Brauker et al. | |
| 5,814,405 A | 9/1998 | Branca et al. | |
| 5,837,234 A | 11/1998 | Yapel et al. | |
| 5,843,069 A | 12/1998 | Butler et al. | |
| 5,882,354 A | 3/1999 | Brauker et al. | |
| 5,980,889 A | 11/1999 | Butler et al. | |
| 6,060,640 A | 5/2000 | Pauley et al. | |
| 6,143,293 A | 11/2000 | Calvert et al. | |
| 6,156,305 A | 12/2000 | Brauker et al. | |
| 6,197,575 B1 | 3/2001 | Griffith et al. | |
| 6,562,616 B1 | 5/2003 | Toner et al. | |
| 7,659,219 B2 | 2/2010 | Biran et al. | |
| 7,892,222 B2 | 2/2011 | Bloch et al. | |
| 8,278,106 B2 | 10/2012 | Martinson et al. | |
| 8,518,123 B2 | 8/2013 | Jensen et al. | |
| 8,647,861 B2 | 2/2014 | Ingber et al. | |
| 9,433,557 B2 | 9/2016 | Baetge et al. | |
| 10,695,379 B2 | 6/2020 | Greenwood et al. | |
| 11,033,666 B2 | 6/2021 | Ferrante et al. | |
| 11,446,133 B2 | 9/2022 | Papas | |
| 11,723,558 B2 | 8/2023 | Papas | |
| 2003/0054544 A1 | 3/2003 | Gruenberg | |
| 2003/0087427 A1 | 5/2003 | Colton et al. | |
| 2003/0129736 A1 | 7/2003 | Mitrani | |
| 2004/0010320 A1 | 1/2004 | Huckle et al. | |
| 2004/0024342 A1 | 2/2004 | Weitzel et al. | |
| 2004/0133188 A1 | 7/2004 | Vardi et al. | |
| 2004/0166141 A1 | 8/2004 | Cerami et al. | |
| 2004/0197374 A1 | 10/2004 | Ghabrial et al. | |
| 2005/0136092 A1 | 6/2005 | Rotem et al. | |
| 2005/0221485 A1 | 10/2005 | Bader | |
| 2005/0267440 A1 | 12/2005 | Herman et al. | |
| 2006/0013835 A1 | 1/2006 | Anderson et al. | |
| 2006/0019333 A1 | 1/2006 | Leblanc et al. | |
| 2007/0061015 A1 | 3/2007 | Biris et al. | |
| 2007/0066138 A1 | 3/2007 | Ferrari et al. | |
| 2008/0021436 A1 | 1/2008 | Wolpert et al. | |
| 2009/0074832 A1 | 3/2009 | Zussman et al. | |
| 2009/0110669 A1 | 4/2009 | Schneiderman et al. | |
| 2010/0082114 A1 | 4/2010 | Gingras et al. | |
| 2010/0124564 A1 | 5/2010 | Martinson et al. | |
| 2010/0130916 A1 | 5/2010 | Barkai et al. | |
| 2010/0160760 A1 | 6/2010 | Shults et al. | |
| 2010/0172952 A1 | 7/2010 | Srouji et al. | |
| 2010/0196439 A1 | 8/2010 | Beck et al. | |
| 2010/0228110 A1 | 9/2010 | Tsoukalis | |
| 2010/0240117 A1 | 9/2010 | Ying et al. | |
| 2010/0255059 A1 | 10/2010 | Marquez et al. | |
| 2011/0054589 A1 | 3/2011 | Bashiri et al. | |
| 2011/0092949 A1 | 4/2011 | Wang | |
| 2012/0041355 A1 | 2/2012 | Edman et al. | |
| 2012/0245705 A1 | 9/2012 | Hasilo et al. | |
| 2013/0289540 A1 | 10/2013 | Zeltser et al. | |
| 2013/0344131 A1 | 12/2013 | Lo et al. | |
| 2014/0014226 A1 | 1/2014 | Baetge et al. | |
| 2014/0039383 A1 | 2/2014 | Dobbles et al. | |
| 2014/0051162 A1 | 2/2014 | Nankervis | |
| 2014/0052095 A1 | 2/2014 | Dobbles et al. | |
| 2014/0088347 A1 | 3/2014 | Frigstad et al. | |
| 2014/0257515 A1 | 9/2014 | Green et al. | |
| 2014/0308315 A1 | 10/2014 | Knezevich et al. | |
| 2015/0112247 A1 | 4/2015 | Papas et al. | |
| 2015/0129497 A1 | 5/2015 | Humes et al. | |
| 2015/0273200 A1 | 10/2015 | Rotem et al. | |
| 2015/0320836 A1 | 11/2015 | Itkin-Ansari et al. | |
| 2015/0359472 A1 | 12/2015 | Botvinnick et al. | |
| 2016/0022180 A1 | 1/2016 | Joseph et al. | |
| 2016/0038207 A1 | 2/2016 | Wei et al. | |
| 2016/0082236 A1 | 3/2016 | Botvinick et al. | |
| 2016/0123848 A1 | 5/2016 | Griffin et al. | |
| 2016/0184569 A1 | 6/2016 | Bouche et al. | |
| 2017/0072074 A1 | 3/2017 | Gladnikoff et al. | |
| 2017/0173262 A1 | 6/2017 | Veltz | |
| 2018/0000395 A1 | 1/2018 | Lucisano et al. | |
| 2018/0126134 A1 | 5/2018 | Cully et al. | |
| 2018/0263238 A1 | 9/2018 | Flanagan et al. | |
| 2018/0298343 A1 | 10/2018 | Sivakumaran | |
| 2018/0318566 A1 | 11/2018 | Ferrante et al. | |
| 2018/0344665 A1 | 12/2018 | Isenburg et al. | |
| 2019/0076840 A1 | 3/2019 | Gottardi et al. | |
| 2019/0136176 A1 | 5/2019 | Kawachi et al. | |
| 2019/0211294 A1 | 7/2019 | Karnieli | |
| 2019/0224377 A1 | 7/2019 | Papas | |
| 2019/0336267 A1 | 11/2019 | Tempelman et al. | |
| 2020/0054257 A1 | 2/2020 | Papas | |
| 2020/0063085 A1 | 2/2020 | Papas | |
| 2021/0386333 A1 | 12/2021 | Papas | |
| 2021/0401564 A1 | 12/2021 | Neuenfeldt et al. | |
| 2022/0134074 A1 | 5/2022 | Papas | |
| 2022/0362002 A1 | 11/2022 | Neuenfeldt et al. | |
| 2023/0000612 A1 | 1/2023 | Papas | |

FOREIGN PATENT DOCUMENTS

| | | |
|---|---|---|
| DE | 8909058 | 9/1989 |
| EP | 0344314 | 12/1989 |
| EP | 1351623 | 10/2003 |
| EP | 2508212 | 10/2012 |
| JP | H06-205665 | 7/1994 |
| JP | 2004-530431 | 10/2004 |
| JP | 2014-514942 | 6/2014 |
| KR | 10-2012-0091008 | 8/2012 |
| KR | 10-2014-0023252 | 2/2014 |
| KR | 10-2016-0094391 | 8/2016 |
| WO | WO 91/00119 | 1/1991 |
| WO | WO 01/12158 | 2/2001 |
| WO | WO 02/100335 | 12/2002 |
| WO | WO 2006/106506 | 10/2006 |
| WO | WO 2008/100559 | 8/2008 |
| WO | WO 2010/061387 | 6/2010 |
| WO | WO 2012/136701 | 10/2012 |
| WO | WO 2014/173441 | 10/2014 |
| WO | WO 2015/145264 | 10/2015 |
| WO | WO 2018/067813 | 4/2018 |
| WO | WO 2018/085714 | 5/2018 |
| WO | WO 2018/089397 | 5/2018 |
| WO | WO 2018/102077 | 6/2018 |
| WO | WO 2018/144098 | 8/2018 |
| WO | WO 2018/144099 | 8/2018 |
| WO | WO 2022/094380 | 5/2022 |

OTHER PUBLICATIONS

U.S. Appl. No. 18/225,504, filed Jul. 24, 2023, Papas.
"Membrane Basics," PermSelect—Silicone Gas Exchange Membranes, 2021, retrieved from https://www.permselect.com/membranes, 9 pages.
Carlsson et al., "Transplantation of macroencapsulated human islets within the bioartificial pancreas BAir to patients with type 1 diabetes mellitus," American Journal of Transplantation, vol. 18, 2018, pp. 1735-1744.

(56) References Cited

OTHER PUBLICATIONS

Geller et al., "Use of an Immunoisolation Device for Cell Transplantation and Tumor Immunotherapy," Annals New York Academy of Science, Date Unnknown, 14 pages.
Gholipourmalekabadi et al., "Oxygen-Generatin Biomaterials: A New, Viable Paradigm for Tissue Engineering?" Trends in Biotechnology, vol. 34, No. 12, Dec. 2016, pp. 1010-1021.
Knoepiler, "ViaCyte CEO Paul Laikind Interview: Trial Update, Melton's Concerns, & Future," The Niche, Mar. 2, 2015, retrieved from https://ipscell.com/2015/03/viacyte, 6 pages.
Krishnan et al., "Cellular Immunoisolation for Islet Transplantation by a Novel Dual Porosity Electrospun Membrane," Transplantation Proceedings, vol. 43, No. 9, Nov. 2011, pp. 3256-3261.
Krishnan et al., "Islet And Stem Cell Encapsulation For Clinical Transplantation," Review of Diabetic Studies, vol. 11, No. 1, 2014, pp. 84-101.
Lathuiliere et al., "Encapsulated Cellular Implants for Recombinant Protein Delivery and Therapeutic Modulation of the Immune System," International Journal of Molecular Sciences, vol. 16, 2015, pp. 10578-10600.
Lee et al., "Cytokines in Cancer Immunotherapy," Cancers, vol. 3, 2011, pp. 3856-3893.
Lemons et al., "Biomaterials Science: An Introduction to Materials In Medicine," Elsevier Science, 2004, pp. 88-89, 629, & 642. [best available quality].
Makadia et al., "Poly Lactic-co-Glycolic Acid (PLGA) as Biodegradable Controlled Drug Delivery Carrier," Polymers (Basel), vol. 3, No. 3, Sep. 1, 2011, pp. 1377-1397.
Manickavasagam et al., "Critical Assessment of Implantable Drug Delivery Devices in Glaucoma Management," Jounral of Drug Delivery, vol. 2013, No. 895013, Jul. 2013, 12 pages.
Suszynski et al., "Assessment of Tissue-Engineered Islet Graft Viability by Fluorine Magnetic Resonance Spectroscopy," Transplant Proc., vol. 43, No. 9, Nov. 2011, pp. 3221-3225.
Wang et al., "Overcoming foreign-body reaction through nanotopography: Biocompatibility and Immunoisolation properties of a nanofibrous membrane," Biomaterials, vol. 102, Sep. 30, 2016, pp. 249-258.
International Search Report and Written Opinion for International (PCT) Patent Application No. PCT/US2017/060036, dated Feb. 16, 2018, 14 pages.
Official Action for Australia Patent Application No. 2017355528, dated Aug. 20, 2020, 5 pages.
Official Action for Australia Patent Application No. 2017355528, dated Nov. 16, 2020, 4 pages.
Notice of Acceptance for Australia Patent Application No. 2017355528, dated Mar. 22, 2021, 4 pages.
Official Action for Australia Patent Application No. 2021204321, dated Jun. 6, 2022, 3 pages.
Official Action for Australia Patent Application No. 2021204321, dated Jan. 19, 2023, 4 pages.
Official Action for China Patent Application No. 201780081318.9, dated Feb. 1, 2021, 8 pages.
Official Action for China Patent Application No. 201780081318.9, dated Sep. 1, 2021, 12 pages.
Official Action for China Patent Application No. 201780081318.9, dated Apr. 7, 2022, 22 pages.
Notice of Allowance (with English translation) for China Patent Application No. 201780081318.9, dated Oct. 19, 2022, 6 pages.
Extended European Search Report for Europe Patent Application No. 17866485.0, dated Apr. 25, 2020, 9 pages.
Communication Pursuant to Article 94(3) for Europe Patent Application No. 17866485.0, dated Dec. 28, 2022, 6 pages.
Official Action for Korea Patent Application No. 10-2019-7015936, dated Feb. 22, 2022, 11 pages.
Official Action for Korea Patent Application No. 10-2019-7015936, dated Jul. 25, 2022, 5 pages.
Official Action for Korea Patent Application No. 2019-7015936, dated Nov. 29, 2022, 3 pages.
Official Action for Singapore Patent Application No. 11201905391W, dated Apr. 28, 2023, 4 pages.
International Search Report and Written Opinion for International (PCT) Patent Application No. PCT/US2017/060034, dated Jul. 12, 2018, 9 pages.
Official Action for Australia Patent Application No. 2017396753, dated Jul. 23, 2020, 4 pages.
Official Action for Australia Patent Application No. 2017396753, dated Jan. 27, 2021, 5 pages.
Notice of Acceptance for Australia Patent Application No. 2017396753, dated Apr. 20, 2021, 4 pages.
Official Action for Australia Patent Application No. 202106840, dated Jun. 6, 2022, 3 pages.
Official Action for Australia Patent Application No. 2021206840, dated Jan. 17, 2023, 3 pages.
Official Action for Australia Patent Application No. 2021206840, dated May 1, 2023, 4 pages.
Official Action for Australia Patent Application No. 2021206840, dated May 30, 2023, 3 pages.
Notice of Allowance for Australia Patent Application No. 202106840, dated Jun. 8, 2023, 4 pages.
Official Action for China Patent Application No. 201780081104.1, dated Apr. 2, 2021, 10 pages.
Official Action for China Patent Application No. 201780081104.1, dated Dec. 2, 2021, 11 pages.
Official Action for China Patent Application No. 201780081104.1, dated Jun. 30, 2022, 27 pages.
Intent to Grant (with English translation) for China Patent Application No. 201780081104.1, dated Oct. 19, 2022, 6 pages.
Extended European Search Report for European Patent Application No. 17895433.5, dated Apr. 17, 2020, 7 pages.
Communication Pursuant to Article 94(3) for Europe Patent Application No. 17895433.5, dated Jan. 2, 2023, 4 pages.
Official Action for Korea Patent Application No. 10-2019-7015935, dated Feb. 8, 2022, 9 pages.
Notice of Allowance for Korea Patent Application No. 10-2019-7015935, dated Jul. 25, 2022, 3 pages.
Official Action for Korea Patent Application No. 10-2022-7037085, dated Jun. 20, 2023, 9 pages.
International Search Report and Written Opinion for International (PCT) Patent Application No. PCT/US2017/060014, dated Jul. 10, 2018, 14 pages.
Official Action for Australian Patent Application No. 2017396754, dated Nov. 12, 2020, 7 pages.
Notice of Allowance for Australian Patent Application No. 2017396754, dated Jul. 21, 2021, 4 pages.
Official Action for China Patent Application No. 201780081103.7, dated Jan. 11, 2021, 11 pages.
Official Action for China Patent Application No. 201780081103.7, dated Nov. 1, 2021, 11 pages.
Notice of Allowance for China Patent Application No. 201780081103.7, dated Mar. 23, 2022, 2 pages.
Extended European Search Report for Europe Patent Application No. 17894862.6, dated May 20, 2020, 4 pages.
Communication Pursuant to Article 94(3) for Europe Patent Application No. 17894862.6, dated Feb. 1, 2023, 9 pages.
Official Action for Korea Patent Application No. 10-2019-7015937, dated Jan. 12, 2022, 14 pages.
Notice of Allowance for Korea Patent Application No. 10-2019-7015937, dated May 20, 2022, 6 pages.
Notice of Allowance for Korea Patent Application No. 10-2019-7015937, dated Jul. 22, 2022, 3 pages.
Official Action for Korea Patent Application No. 10-2022-7037086, dated Jun. 15, 2023, 6 pages.
International Search Report and Written Opinion for International (PCT) Patent Application No. PCT/US2017/060043, dated Jun. 14, 2018, 9 pages.
Official Action for Australi Patent Application No. 2017366791, dated Jun. 22, 2020, 4 pages.
Notice of Allowance for Australia Patent Application No. 2017366791, dated Jan. 8, 2021, 4 pages.
Official Action for Australia Patent Application No. 2021202373, dated Oct. 24, 2022, 7 pages.

(56) References Cited

OTHER PUBLICATIONS

Official Action for China Patent Application No. 201780081105.6, dated Aug. 9, 2021, 12 pages.
Official Action for China Patent Application No. 201780081105.6, dated Mar. 24, 2022, 12 pages.
Official Action for China Patent Application No. 201780081105.6, dated Sep. 29, 2022, 8 pages.
Official Action (with English summary) for China Patent Application No. 201780081105.6, dated Apr. 18, 2023, 8 pages.
Extended European Search Report for Europe Patent Application No. 17875181.4, dated Apr. 28, 2020, 4 pages.
Communication Pursuant to Article 94(3) for Europe Patent Application No. 17875181.4, dated Feb. 9, 2023, 6 pages.
Official Action for Korea Patent Application No. 10-2019-7015938, dated Sep. 30, 2021, 5 pages.
Official Action (no English translation available) for Korea Patent Application No. 10-2022-7028922, dated Feb. 3, 2023, 5 pages.
Official Action for Singapore Patent Application No. 11201905390Q, dated Apr. 28, 2023, 3 pages.
International Search Report and Written Opinion for International (PCT) Patent Application No. PCT/US2019/052728, dated Dec. 13, 2019, 10 pages.
International Preliminary Report on Patentability for International (PCT) Application No. PCT/US2019/052728, dated Apr. 1, 2021, 9 pages.
Official Action for Australia Patent Application No. 2019346547, dated Feb. 9, 2022, 4 pages.
Official Action for Australia Patent Application No. 2019346547, dated Sep. 2, 2022, 4 pages.
Official Action for Australia Patent Application No. 2019346547, dated Jan. 13, 2023, 6 pages.
Official Action for Canada patent Application No. 3114197, dated Jun. 6, 2022, 6 pages.
Notice of Allowance for Canada Patent Application No. 3114197, dated Apr. 17, 2023, 1 page.
Partial Supplementary European Search Report for Europe Patent Application No. 19867716.3, dated May 23, 2022, 13 pages.
Extended European Search Report for Europe Patent Application No. 19867716.3, dated Oct. 6, 2022, 12 pages.
Official Action for India Patent Application No. 202117012735, dated Feb. 11, 2022, 5 pages.
Official Action (with English summary) for Japan Patent Application No. 2021-540389, dated Jun. 21, 2022, 7 pages.
Official Action (with English summary) for Japan Patent Application No. 2021-540389, dated Jan. 17, 2023, 6 pages.
Official Action (with English translation) for Korea Patent Application No. 10-2021-7012313, dated Mar. 3, 2023, 17 pages.
Official Action for Taiwan Patent Application No. 108134435, dated Jul. 18, 2023, 11 pages.
Invitation to Pay Additional Fees for International (PCT) Patent Application No. PCT/US2021/057526, dated Jan. 5, 2022, 3 pages.
International Search Report and Written Opinion for International (PCT) Patent Application No. PCT/US2021/057526, dated Mar. 2, 2022, 16 pages.
International Preliminary Report on Patentability for International (PCT) Application No. PCT/US2021/057526, dated May 11, 2023, 9 pages.
Official Action for U.S. Appl. No. 16/647,338, dated Jun. 16, 2022, 10 pages.
Official Action for U.S. Appl. No. 16/647,338, dated Dec. 15, 2022, 9 pages.
Notice of Allowance for U.S. Appl. No. 16/647,338, dated Mar. 24, 2023, 7 pages.
Official Action for U.S. Appl. No. 16/347,388, dated May 11, 2021, 10 pages.
Official Action for U.S. Appl. No. 16/347,388, dated Oct. 4, 2021, 10 pages.
Notice of Allowance for U.S. Appl. No. 16/347,388, dated May 12, 2022, 10 pages.
Corrected Notice of Allowance for U.S. Appl. No. 16/347,388, dated May 20, 2022, 6 pages.
Official Action for U.S. Appl. No. 16/347,147, dated Apr. 8, 2021, 8 pages. Restriction Requirement.
Official Action for U.S. Appl. No. 16/347,147, dated Jul. 2, 2021, 12 pages.
Official Action for U.S. Appl. No. 16/347,147, dated Nov. 12, 2021, 11 pages.
Official Action for U.S. Appl. No. 16/347,147, dated Jun. 2, 2022, 14 pages.
Official Action for U.S. Appl. No. 16/347,147, dated Jan. 10, 2023, 15 pages.
Notice of Allowance for U.S. Appl. No. 16/347,147, dated Apr. 17, 2023, 7 pages.
Corrected Notice of Allowance for U.S. Appl. No. 16/347,147, dated Apr. 20, 2023, 2 pages.
Official Action for U.S. Appl. No. 16/347,160, dated Dec. 28, 2020, 15 pages.
Official Action for U.S. Appl. No. 16/347,160, dated Nov. 29, 2021, 14 pages.
Official Action for U.S. Appl. No. 16/347,160, dated Jul. 7, 2022, 14 pages.
Official Action for U.S. Appl. No. 16/347,160, dated Dec. 19, 2022, 19 pages.
Official Action for U.S. Appl. No. 17/387,595, dated Nov. 10, 2021, 15 pages.
Official Action for U.S. Appl. No. 17/387,595, dated Mar. 28, 2022, 18 pages.
Official Action for U.S. Appl. No. 17/387,595, dated Dec. 19, 2022, 20 pages.
Official Action for U.S. Appl. No. 17/387,595, dated Apr. 10, 2023, 29 pages.
Official Action for U.S. Appl. No. 17/876,302, dated Oct. 25, 2022, 22 pages.
Official Action for U.S. Appl. No. 17/876,302, dated Apr. 3, 2023, 19 pages.
Official Action for U.S. Appl. No. 17/516,179, dated Jul. 11, 2023, 8 pages. Restriction Requirement.
Official Action (with English translation) for China Patent Application No. 201980062844.X, dated Aug. 12, 2023, 30 pages.

\* cited by examiner

METHODS AND SYSTEMS FOR REAL-TIME ASSESSMENT OF CELLS IN ENCAPSULATION DEVICES PRE-AND POST-TRANSPLANTATION

CROSS REFERENCE

This U.S. Non-Provisional patent application is a Continuation of U.S. patent application Ser. No. 16/347,147, filed on May 2, 2019, which is a national stage application under 35 U.S.C. 371 and claims benefit of PCT Application No. PCT/US2017/060041 having an international filing date of Nov. 3, 2017, which designated the United States, which PCT application claimed the benefit and priority to U.S. Patent Application No. 62/417,039, filed Nov. 3, 2016, the specification(s) of which is/are incorporated herein in their entirety by reference.

FIELD OF THE INVENTION

The present invention relates to methods and systems for assessing in real-time various parameters of cells housed in encapsulation devices. Parameters may include insulin secretion levels and oxygen consumption rates or any other appropriate parameter.

BACKGROUND OF THE INVENTION

It can be important to know whether or not cells in an encapsulation device are healthy and viable and functional both before the cells are transplanted and after the cells are transplanted. The present invention features methods and systems for monitoring cells (e.g., cell viability, function, etc., e.g., via measuring oxygen consumption rates, insulin secretion levels, tee.) in an encapsulation device in real-time before and after transplantation. The present invention also features methods of helping to reduce cell damage (e.g., ischemic damage, physical damage, etc.) during the loading process of an encapsulation device, e.g., before implantation, before and during storage, etc.

The present invention may be usable for other cell types (not just for diabetes treatment). For example, cells may include hepatocyte for bio artificial liver, heart cells, muscle cells, etc.

The disclosures of the following U.S. patents are incorporated in their entirety by reference herein: U.S. Pat. No. 5,713,888; U.S. Pat. App. No. 2003/0087427.

SUMMARY OF THE INVENTION

The present invention features systems, e.g., systems for measuring oxygen consumption rate (OCR) of cells, or measuring other features such as insulin secretion, pH, lactate, CO2 levels, etc. In some embodiments, the system comprises a bioreactor with an inlet and an outlet, wherein a first oxygen sensor is disposed at the inlet and a second oxygen sensor is disposed at the outlet; an encapsulation device comprising a lumen with the cells, and a vascularizing membrane, the encapsulation device is housed in the bioreactor; a combined heat and gas exchanger for heating liquid media to at least one temperature from 7° C. to 27° C. (or from 7° C. to 37° C.) and for allows oxygen to be controlled from O to 100%; and a pump for pumping liquid media from the heat exchanger to the bioreactor via the inlet and out the outlet. Oxygen sensors detect oxygen levels of the media for determining oxygen consumption rate of the cells.

In some embodiments, the bioreactor is encased in an incubator that can adjust and control temperature and oxygen, e.g. a temperature from 4-40 C, oxygen level from 0 to 100%.

In some embodiments, the system comprises a sample removal outlet for obtaining a media sample after the outlet of the bioreactor. The media sample may be for measuring insulin secretion. In some embodiments, the gas exchanger or combined heat and gas exchanger provides oxygen to the media. In some embodiments, oxygen production in the media can be shut off.

In some embodiments, the media sample is for measuring insulin, glucagon, pancreatic polypeptide, c-peptide, a hormone, or a combination thereof. In some embodiments, the media sample is for measuring chemical release (secretion) as affected by a variety of secretagogues and chemical agents that can be introduced in the system (such as glucose, arginine, KCI, GLP-1).

In some embodiments, the cells are islet cells or stem cell-derived beta cells. In some embodiments, the system comprises a glucose sensor, a lactate sensor, a pH sensor, a CO2 sensor, or a combination thereof. In some embodiments, the oxygen sensors are operatively connected to a system for regulating an amount of oxygen delivered to the cells. In some embodiments, the system for regulating an amount of oxygen delivered to the cells can adjust a level of oxygen supplied to the cells based on a command received based on an oxygen level determined by the oxygen sensors.

The present invention also features methods for measuring oxygen consumption rate (OCR) of cells or other features (e.g., insulin secretion, etc., as described herein). The method may comprise pumping media at a temperature from 7° C. to 27° C. through a system comprising: a bioreactor with an inlet and an outlet, wherein a first oxygen sensor is disposed at the inlet and a second oxygen sensor is disposed at the outlet; and an encapsulation device comprising a lumen with the cells, and a vascularizing membrane, the encapsulation device is housed in the bioreactor; wherein the oxygen sensors detect oxygen levels of the media for determining oxygen consumption rate of the cells.

In some embodiments, the heat exchanger is separate from the gas exchanger. In some embodiments, the heat exchanger is combined with the gas exchanger.

The present invention also features methods for measuring oxygen consumption rate (OCR) of cells or other features (e.g., insulin secretion, etc., as described herein). The method may comprise pumping media at a temperature from 7° C. to 27° C. through a system according to the present invention; wherein the oxygen sensors detect oxygen levels of the media for determining oxygen consumption rate of the cells.

The present invention also features methods of measuring viability of cells. In some embodiments, the method comprises (in system with an encapsulation device with cells receiving exogenous oxygen, said cells comprising islet cells or stem cell-derived beta cells), discontinuing delivery of exogenous oxygen to the cells; setting the temperature of the cells in the encapsulation device to a temperature from 7° C. to 27° C.; and measuring oxygen consumption rate (OCR), wherein a certain OCR level is indicative of the presence of viable cells.

The present invention also features methods of measuring viability of cells. In some embodiments, the method comprises (in system with an encapsulation device with cells receiving exogenous oxygen, said cells comprising islet cells or stem cell-derived beta cells), discontinuing delivery of exogenous oxygen to the cells; setting the temperature of the cells in the encapsulation device to a temperature from 7° C. to 27° C.; and measuring oxygen consumption rate (OCR), wherein an certain OCR level is indicative of the presence of enough viable cells for implantation of the encapsulation device.

In some embodiments, the aforementioned methods comprise raising the temperature to 37° C., and measuring glucose-stimulated insulin secretion (GSIS) of the cells. In some embodiments, the aforementioned methods comprise raising the temperature to 37° C., and measuring glucose-stimulated insulin secretion (GSIS) of the cells, wherein an insulin secretion level within a threshold level or above a threshold level are indicative of the presence of enough viable and functional cells for implantation of the encapsulation device.

Other parameters include the release (secretion by the cells) of other chemical, hormone/polypetide release (such as glucagon, c-peptide, pancreatic polypeptide) which can be induced or inhibited by secretagogues or other chemical agents (such as glucose, arginine, KCl, GLP-1).

In some embodiments, an oxygen sensor is disposed at both an inlet and an outlet of a bioreactor holding an encapsulation device with the cells. In some embodiments, the system further comprises a glucose sensor, a lactate sensor, a pH sensor, a CO2 sensor, or a combination thereof.

The present invention also features a method of loading cells into an encapsulation device receiving exogenous oxygen (the cells comprising islet cells or stem cell-derived beta cells). In some embodiments, the method comprises lowering the temperature of the encapsulation device to a particular low temperature (e.g., 4 to 8 C, 7 to 15 C, etc.); and loading cells into the encapsulation device via a cell loading port, wherein the low temperature helps minimize ischemic or physical damage to the cells.

In some embodiments herein, exogenous oxygen is delivered to the device at a level of about 40% oxygen.

In some embodiments, the encapsulation device is held in a reservoir, said reservoir adapted to hold the encapsulation device in media. In some embodiments, the encapsulation device comprises tubing for providing cooling medium or oxygen to one or more layers of cells. In some embodiments, the oxygen sensors are operatively connected to a system for regulating exogenous delivery of oxygen to the cells.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which.

DETAILED DESCRIPTION OF THE INVENTION

Encapsulation Devices

Figure 1A:
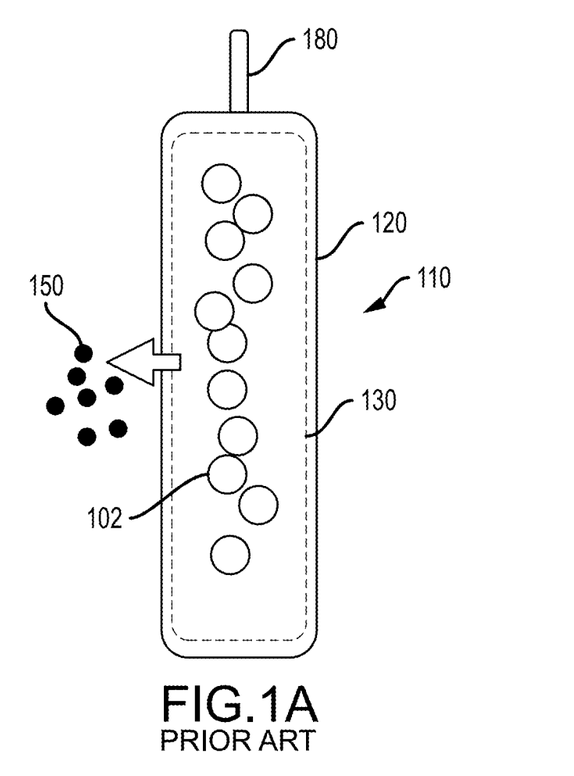
FIG. 1A shows an example of a single-chamber encapsulation device for holding cells or tissues. The device comprises a port to access the lumen for loading the cells or tissue.
Figure 1B:
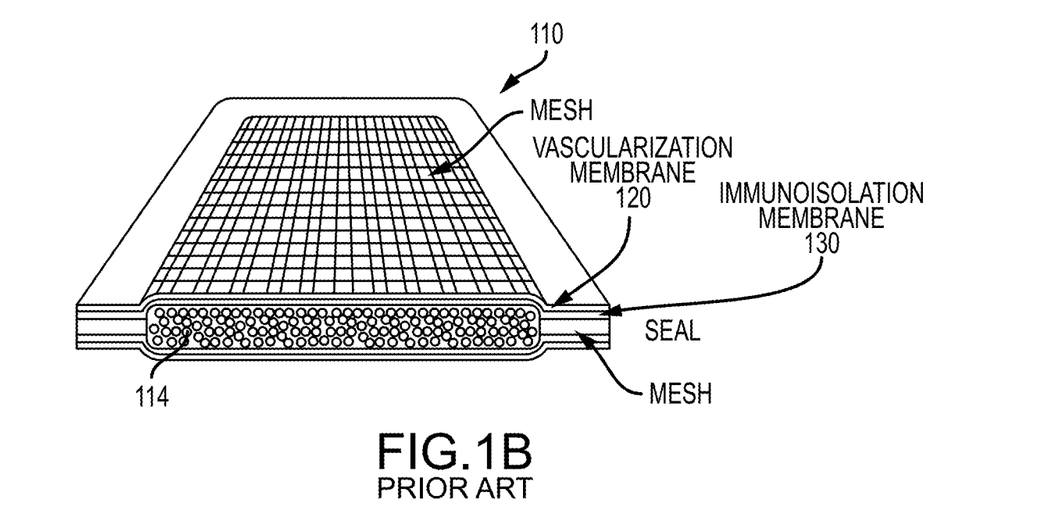
FIG. 1B shows a cross-sectional view of the device of FIG. 1A. The cells are encapsulated in a two-layer membrane envelope formed using a mesh insert. The device comprises a vascularization membrane and an immunoisolation membrane. The present invention is not limited to devices that utilize an immunoisolation membrane: in some embodiments, the device only comprises the vascularization membrane.

Encapsulation devices are devices for holding cells or tissues. The encapsulation device (110) shown in FIG. 1A is a single-chamber encapsulation device. The device (110) comprises an inner lumen for holding the cells (102) or tissue and at least one membrane, e.g., a vascularization membrane (120), which is impermeable to cells. In some embodiments, the device (100) further comprises an immunoisolation membrane (130). Non-cell factors or molecules (150) can escape the cell impermeable membrane. The device (110) also comprises a port (180) to access the lumen for loading the cells or tissue. FIG. 1B shows a cross-sectional view of an encapsulation device. The cells are encapsulated in a lumen (114) by a two-layer membrane envelope, a vascularization membrane (120) and an immunoisolation membrane (130). The device (110) also has structural support, e.g., mesh, seals, etc. Vasculature may grow around the device (110).

In some embodiments, the encapsulation devices (110) comprise a vascularization membrane (120) and immunoisolation membrane (130). In some embodiments, the encapsulation devices (110) comprise just the vascularization membrane (120). This allows blood vessels to grow within the transplanted tissue.

In the examples shown in FIG. 1A and FIG. 1B, the cells therein are about 5-15 μm in diameter. The outer membrane, the vascularization membrane (120), has a pore size from 5-10 μm. The vascularization membrane (120) is about 15 μm thick. The immunoisolation membrane (130) has a pore size of about 0.4 μm. The immunoisolation membrane (130) is about 30 μm thick. In some embodiments, the membranes (120, 130) are constructed from materials such as polytetraflouroethylene (PTFE) or other similar material. The present invention is not limited to the aforementioned pore sizes and thicknesses of the membranes used therein. The present invention is not limited to the aforementioned materials.

The encapsulation devices (110) may be constructed in various shapes and sizes and with various lumen volumes. For example, in some embodiments, the lumen has a volume of about 4.5 µl. In some embodiments, the lumen has a volume of 20 µl. In some embodiments, the lumen has a volume of 40 µl. In some embodiments, the device (110) is from 4 to 5 cm in length. In some embodiments, the device (110) is from 2 to 5 cm in length, e.g., 3 cm. In some embodiments, the device (110) is from 5 to 10 cm in length. The present invention is not limited to the aforementioned dimensions and lumen volumes. For example, in some embodiments, the lumen has a volume of about 100 µl. In some embodiments, the lumen has a volume of about 200 µl. In some embodiments, the lumen has a volume from 2 to 50 µl. In some embodiments, the lumen has a volume from 10 to 100 µl. In some embodiments, the lumen has a volume from 40 to 200 µl. In some embodiments, the lumen has a volume from 100 to 300 µl. In some embodiments, the lumen has a volume from 200 to 500 µl.

Figure 2A:
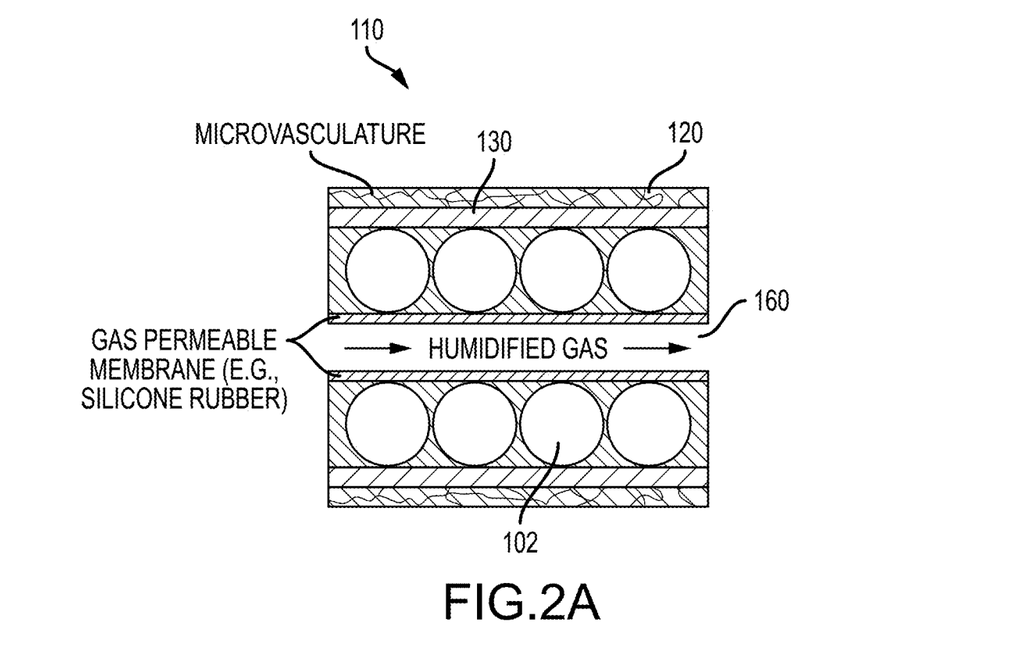
FIG. 2A shows a detailed view of an encapsulation device with an immunoisolation membrane. The device features two chambers or lumens separated by a gas channel.
Figure 2B:
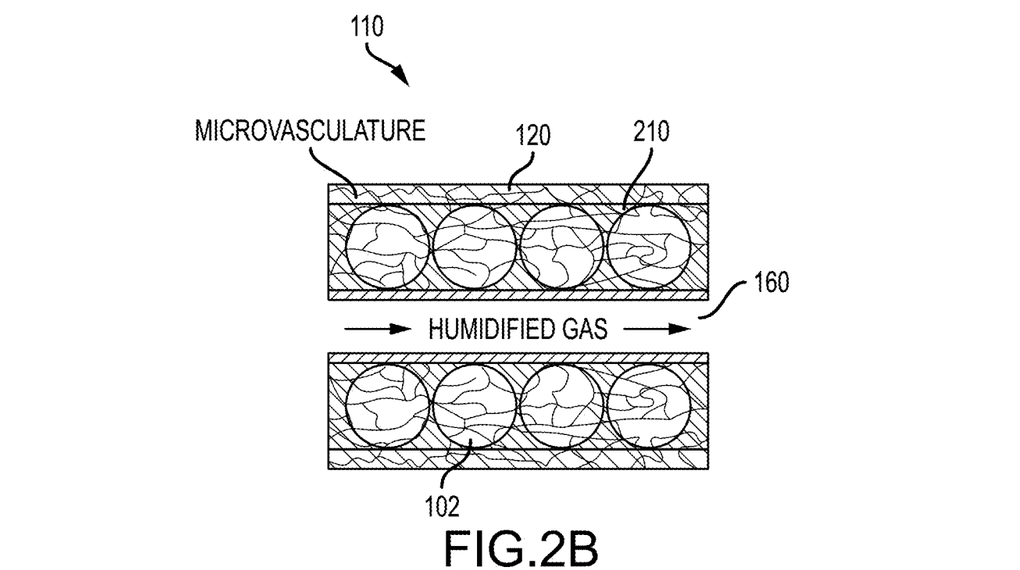
FIG. 2B shows a detailed view of an encapsulation device without the immunoisolation membrane. The device features two chambers or lumens separated by a gas channel.

In some embodiments, within the encapsulation devices (110), there may be layers of cells or tissue, e.g., multiple lumens within the device (110). For example, an encapsulation device (110) may comprise two chambers or lumens. In some embodiments, the device comprises more than two chambers or lumens, e.g., 3 chambers or lumens, 4 chambers or lumens, 5 chambers or lumens, etc. FIG. 2A and FIG. 2B show examples of an encapsulation with two lumens (two chambers) that are separated by a gas channel (160). FIG. 2A and FIG. 2B also show vascularizing membrane and microvasculature. The blood vessels embed into the vascularizing membrane.

In some embodiments, the chamber or lumen comprises a single layer of cells. In some embodiments, the chamber or lumen comprises two layers of cells. In some embodiments, the chamber comprises three or more layers of cells. In some embodiments, islet spheroids (about 150 µm in size) are used (shown in FIG. 2A, FIG. 2B). In some embodiments, a dual layer of the islet spheroids is used (lumen thickness would be about 300 µm in the chamber or in each chamber). In some embodiments, a third layer is supported depending on the metabolic activity and other characteristics of the spheroids/cells used. Note spheroids may not be touching each other in some configurations and the space between them may be 1 or 2 spheroids apart (e.g., 150 µm, 300 um), or more or less.

Methods and Systems for Monitoring Cells

Figure 3A:
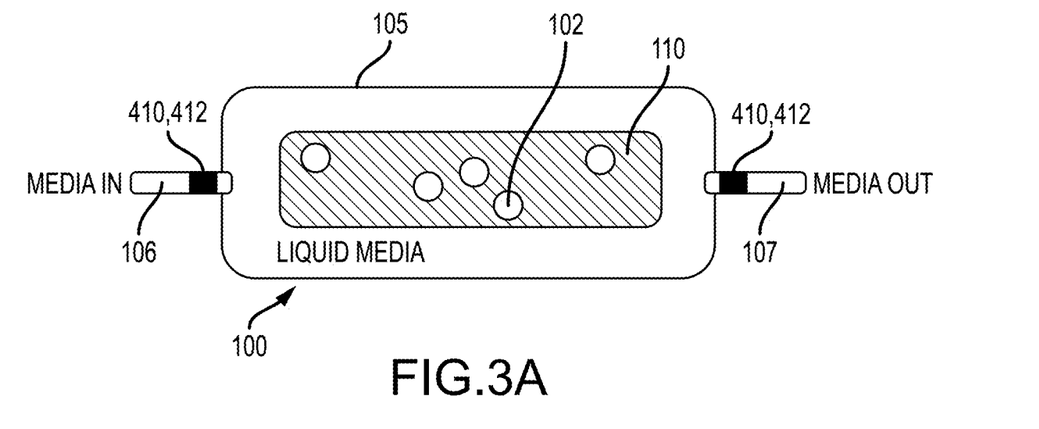
FIG. 3A shows a schematic view of a system comprising a bioreactor and encapsulation device with cells disposed therein. Liquid media flows in via an inlet (which may comprise a flow cell with an oxygen sensor) and flows out of an outlet (which may comprise a flow cell with an oxygen sensor). In some embodiments, the encapsulation device is a single chamber device. In some embodiments, the encapsulation device is a dual chamber device with a gas channel (e.g., oxygen channel) disposed between the chambers (e.g., to allow for higher density). In some embodiments, the sensors on the inlet and outlet are for oxygen consumption rate measurements (which may be used as a means of evaluating viability of the device with cells).

FIG. 3A shows a schematic view of a system (100) comprising a bioreactor and encapsulation device with cells disposed therein. Liquid surrounds the encapsulation device (110). In some embodiments, the encapsulation device is a single chamber device. In some embodiments, the encapsulation device is a dual chamber device with a gas channel (e.g., oxygen channel) disposed between the chambers (e.g., to allow for higher density). Liquid media flows in via an inlet (106) (which may comprise a flow cell (412) with an oxygen sensor (410)) and flows out of an outlet (107) (which may comprise a flow cell (412) with an oxygen sensor (410)). In some embodiments, the sensors on the inlet and outlet are for oxygen consumption rate measurements (which may be used as a means of evaluating viability and health of the cells).

Figure 3B:
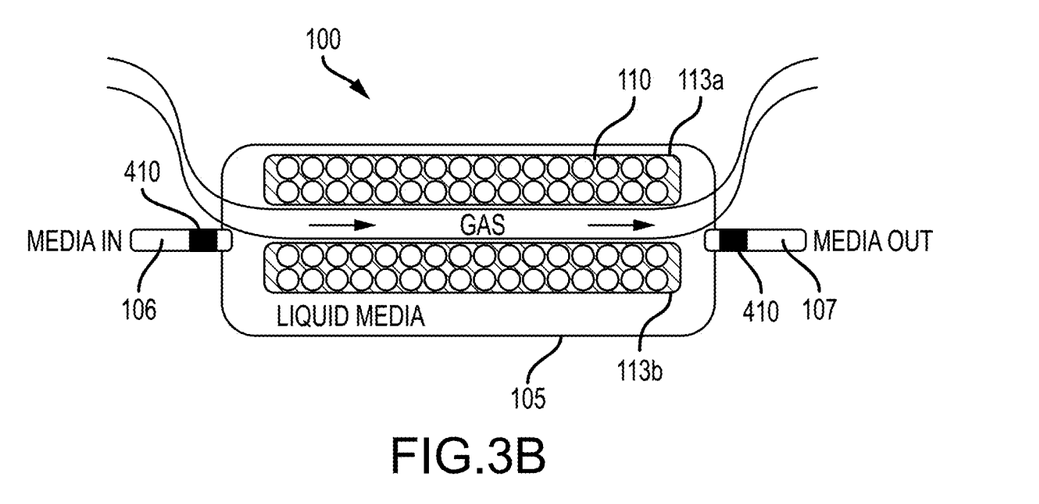
FIG. 3B shows a schematic view of a dual chamber device that may be present in a system of FIG. 3A. The gas channel may be sealed or gas may be vented through the tubing of the gas channel.

FIG. 3B shows a schematic view of a system that comprises a dual chamber device (e.g., used in a system shown in FIG. 3A) having a first chamber (113a) and a second chamber (113b) separated by a gas channel (160). Gas (e.g., air, oxygen) is delivered through the middle of the chambers via the gas channel to support viability and function of the cells. The gas channel does not leak into the media of the bioreactor, and does not cause leakage of the media in the bioreactor (it is separate from the media and inlet/outlet of the bioreactor).

Insulin secretion requires physiological temperature, so the evaluation of cells in the device for insulin secretion needs to be done at 37° C. (assessments at lower temperatures are not accurate).

Oxygen consumption rate (OCR) cannot be accurately evaluated with gas flowing through the gas channel. For OCR, gas flow needs to stop, but the temperature is reduced so that there is sufficient oxygen to the cells in the center of the device and the OCR is not oxygen limited.

OCR measurements may be performed at temperatures at temperature below 37° C. (e.g., 7° C. to 27° C., e.g., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., etc.). Temperature may be adjusted to lower values as a function of metabolic activity and cell density within the devices. OCR is predictably dependent on temperature so that the health of the cells can still be estimated by appropriate temperature correction (Arrhenius type relationship). For example, OCR declines predictably with decreasing temperature in the range of 7° C. to 37° C.

Figure 4:
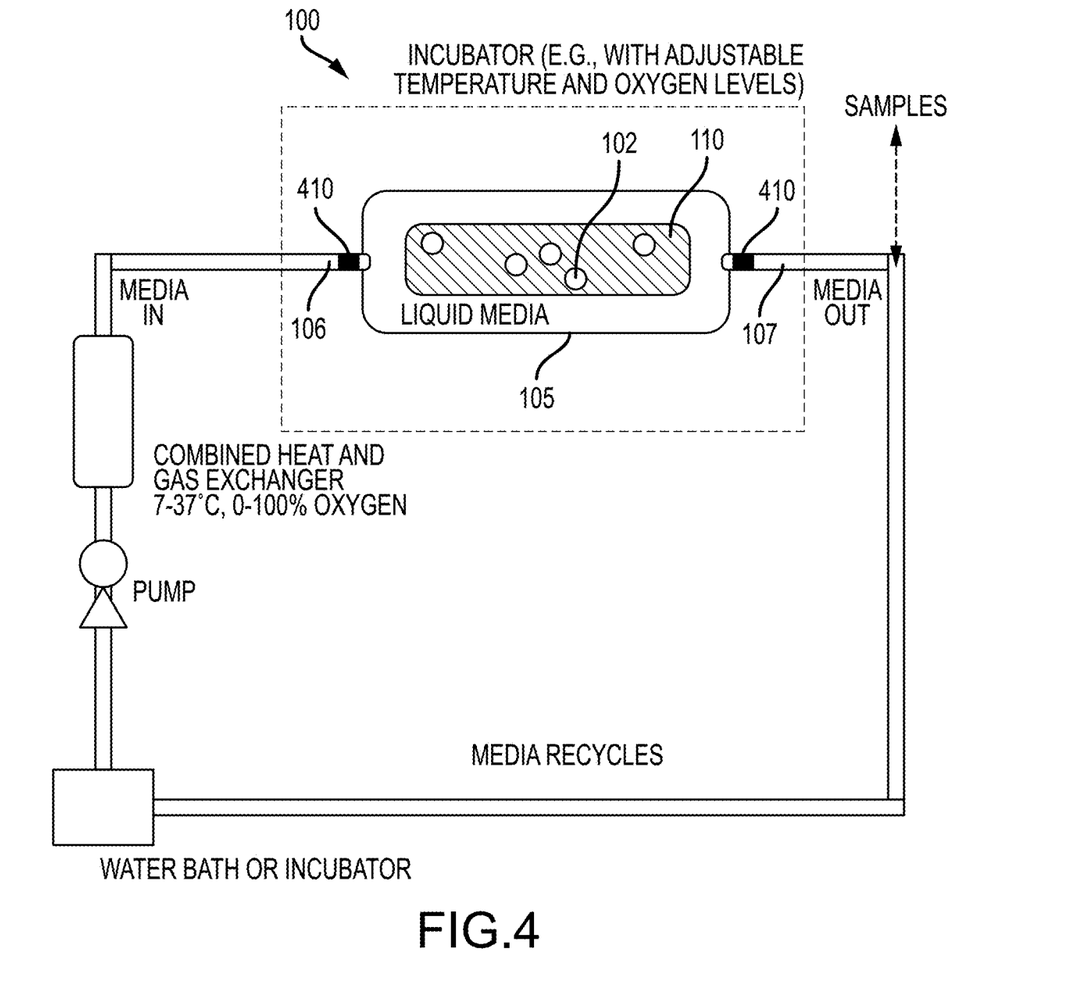
FIG. 4 is a schematic view of a system of the present invention.

FIG. 4 is a schematic view of a system of the present invention. A bioreactor (105) houses an encapsulation device (110), e.g., a single chamber, a dual chamber, etc., with cells. Media may be pumped via a pump through a heat or gas exchanger (or combined heat and gas exchanger), which may bring the media to a particular temperature and to a particular oxygen level. Media then flows through the inlet (106) and through an oxygen sensor (410), through the bioreactor (105) and out the outlet (107) and through the other oxygen sensor (410). Samples (for insulin secretion evaluation) may be obtained from a point outside of the outlet. The media may, for example, be recycled and flow through a water bath or incubator. Or, the media may be discarded.

In some embodiments, the combined heat and gas exchanger (or the separate heat exchanger) heats the media to a temperature between 7° C. to 37° C. (Evaluation of insulin secretion may be performed at 37° C., and then the temperature may be lowered for OCR measurements.) In some embodiments, the gas exchanger oxygenates the media to a percentage from 0-100% (e.g., 40%). Oxygen levels may be selected depending on the amount of exposure time.

For insulin secretion function measurements, high oxygen (e.g., 40% oxygen) may be present in the middle of the dual cell chamber device (along with a temperature of 37° C.).

For oxygen consumption rate (OCR) measurements, no gas is provided to the middle of the dual cell chamber. Temperature is reduced (e.g., to a temperature between 7° C. and 17° C.).

The present invention features methods and systems for monitoring cells (e.g., cell viability, oxygen consumption rates, insulin secretion levels, etc.) in an encapsulation device in real-time before transplantation (e.g., during storage) and/or after transplantation. FIG. 3 and FIG. 4 show examples of systems and devices for storing cells in encapsulation devices. These devices may be equipped with sensors (410) and readers and other features to help with real-time measurements of parameters of the cells to determine cell viability.

In some embodiments, the media is at a temperature from 4 to S° C., e.g., 4° C., 5° C., 6° C., 7° C., S° C. In some embodiments, the media is at a temperature from 2 to S° C. In some embodiments, the media is at a temperature from 4 to 10° C. In some embodiments, the media is at a temperature from 2 to 15° C. In some embodiments, the media is at a temperature from 10 to 20° C. In some embodiments, the media is at a temperature from 20 to 30° C. In some embodiments, the media is at a temperature from 30 to 3S° C. In some embodiments, the oxygen levels are around 40%. In some embodiments, the oxygen levels are less than 40% or more than 40%. In some embodiments, the oxygen level is from 0-5%. In some embodiments, the oxygen level is from 5-15%. In some embodiments, the oxygen level is from 15-25%. In some embodiments, the oxygen level is from 25-35%. In some embodiments, the oxygen level is from 35-40%. In some embodiments, the oxygen level is from 40-50%. In some embodiments, air is used (e.g., oxygen level is about 21%). The present invention is not limited to these temperatures or oxygen levels. Oxygen levels may vary as well. In some embodiments, a particular oxygen level is used initially and then the oxygen level is increased or decreased at a later time. In some embodiments, oxygen is turned on and then off. In some embodiments, oxygen is turned off and then on. In some embodiments, oxygen is turned on and off in a cycle for a period of time or indefinitely.

One or more sensors (e.g., two sensors, three sensors, four sensors, etc.) are integrated into the system, e.g., operatively connected to the encapsulation device or positioned appropriately in proximity to the encapsulation device. The sensors can help measure oxygen consumption rates, insulin secretion level, glucose levels, lactate levels, pH levels, carbon dioxide levels, or a combination thereof.

For example, in some embodiments, a first oxygen sensor is disposed at an inlet of the encapsulation device and a second oxygen sensor is disposed at an outlet of the encapsulation device, wherein the two sensors are used for oxygen consumption rate (OCR) measurements. For example, the difference in pO2 between the first oxygen sensor and the second oxygen sensor can be used to determine OCR of the encapsulated cells. This is a measure of tissue viability.

The sensors (e.g. oxygen sensors) may be used to help determine when the cells are dead (e.g., via oxygen sensors, etc.). Without wishing to limit the present invention to any theory or mechanism, cells are likely dead if there is generally no difference in oxygen levels inside and outside the device. Typically there is a difference (a gradient) in oxygen levels between the inside and outside of the device because oxygen is being consumed by live cells. Thus, no difference would be indicative of no oxygen consumption, thus the cells are likely dead. A bigger difference (gradient) in oxygen levels between the inside and outside of the device would indicate there are more viable cells. A user may determine how many cells are dying by determining the change in oxygen gradient.

The flow of oxygen gas into the encapsulation device can interfere with OCR measurements of the cells. Thus, the methods of the present invention comprise ceasing oxygen gas delivery to the cells. The methods for measuring OCR further comprise reducing the temperature of the encapsulation device and/or media surrounding the device to a temperature between 4 and 8 degrees C., which can help reduce metabolic rate of the cells and thus reduce their oxygen requirements (allowing the oxygen gas delivery to be shut off). The OCR measurements may be continuous. Without wishing to limit the present invention to any theory or mechanism, it is believed that keeping the temperature low during OCR measurements can help improve accuracy of the measurements since OCR measurements at higher temperatures can be affected by the depletion of oxygen within the packed cells due to the higher oxygen consumption be these cells at higher temperatures.

Measurements of potency of cells, e.g., measurements of glucose-stimulated insulin secretion (GSIS) may be made when the cells are at a temperature of about 37° C., or a temperature from 34 to 40° C. (e.g., 34° C., 35° C., C, 36° C., 37° C., 38° C., 39° C., 40° C.).

Insulin can be measured every minute or at shorter intervals or longer intervals as appropriate. Methods of measuring GSIS are known to one of ordinary skill in the art. Without wishing to limit the present invention to any theory or mechanism, it is believed that the flow of oxygen gas in the encapsulation device may be critical for proper GSIS measurements.

The present invention also features methods of helping to reduce cell damage (e.g., ischemic damage, physical damage, etc.) during loading of an encapsulation device. In some embodiments, the methods feature reducing the temperature of the cells, e.g., to a temperature from 4 to 8 degrees C. (which reduces the metabolic rate of cells). The cells may be in a media such as a conventional culture media such as serum supplemented or human serum albumin (HSA) supplemented RPMI, DMEM, or any other appropriate media. The methods may feature delivering oxygen gas to the device and or media. In some embodiments, pluronic acid is used during loading in order to avoid cell damage. This may be beneficial for optimization of cell loading. Also, it is possible that OCR measurements at low temperatures (e.g., from 4 to 8 degrees C.) may help determine the number of viable cells in a device during loading.

The disclosures of the following U.S. Patents are incorporated in their entirety by reference herein: PCT/US2011/055157.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A system for measuring an oxygen consumption rate of cells, the system comprising:
   a bioreactor comprising a first inlet and a first outlet, and a fluid media provided within the bioreactor;
   a first oxygen sensor provided proximal to the first inlet and a second oxygen sensor provided proximal to the first outlet, wherein the first oxygen sensor and the second oxygen sensor are operable to detect oxygen levels of the fluid media and an oxygen consumption rate within the bioreactor based on a difference in oxygen measurements between the first oxygen sensor and the second oxygen sensor;
   an implantable encapsulation device provided within and removable from the bioreactor, the encapsulation device being implantable within a patient, the encapsulation device comprising a channel, a lumen operable to receive cells, and a vascularization membrane at least partially encapsulating the lumen during and after implantation into the patient, wherein the viability of the cells is determinable during and after implantation into the patient, wherein the cells are operable to be at or above a pre-determined threshold for cell viability when the encapsulation device is implanted into the patient;
   wherein the channel extends through the bioreactor and the encapsulation device, wherein the channel is configured to extend along and adjacent to the lumen, wherein the channel is partitioned from the fluid media of the bioreactor;
   a gas exchanger provided between the first outlet and first inlet of the bioreactor operable to provide oxygen to the fluid media within the bioreactor; and
   a pump for pumping and recirculating the fluid media from the first outlet of the bioreactor to the gas exchanger and the first inlet of the bioreactor and a third sensor provided proximal to the first inlet and a fourth sensor provided proximal to the first outlet, wherein the third sensor and the fourth sensor are operable to measure glucose-stimulated insulin secretion within the bioreactor.

2. The system of claim 1, wherein the bioreactor comprises a second inlet and a second outlet for the channel, wherein the second inlet and the second outlet are spaced apart and separate from the first inlet and the first outlet.

3. The system of claim 1, wherein the bioreactor comprises a reservoir housing the fluid media.

4. The system of claim 1, further comprising a sample removal outlet downstream of the first outlet of the bioreactor.

5. The system of claim 1, wherein a closed loop is provided between the first outlet and the first inlet.

6. The system of claim 1, wherein the bioreactor comprises an incubator operable to adjust and control at least one of a temperature and an oxygen concentration of a fluid.

7. The system of claim 1, wherein the pre-determined threshold for cell viability during and after the encapsulation device is implanted into the patient is defined for at least one of an oxygen consumption rate of the cells within the encapsulation device or a level of glucose-stimulated insulin secretion by the cells within the encapsulation device.

8. The system of claim 1, wherein the bioreactor comprises a heat exchanger between the first outlet and first inlet of the bioreactor operable to provide thermal energy to the fluid media within the bioreactor.

9. The system of claim 1, wherein the third and fourth sensors are operatively connected to the implantable encapsulation device.

* * * * *